United States Patent [19]
Kameno et al.

[11] Patent Number: 5,656,153
[45] Date of Patent: Aug. 12, 1997

[54] WATER-REMOVAL CONTROL SYSTEM WITH TIMER DISPLAY FOR DIALYSIS DEVICE

[75] Inventors: Masahiro Kameno, Hirakata; Junichi Kawashita, Takatsuki, both of Japan

[73] Assignee: Nissho Corporation, Osaka-fu, Japan

[21] Appl. No.: 468,039

[22] Filed: Jun. 6, 1995

[30] Foreign Application Priority Data

Jun. 19, 1994 [JP] Japan .................. 6-152627

[51] Int. Cl.⁶ .................. B01D 61/32; B01D 61/30
[52] U.S. Cl. .................. 210/97; 210/138; 210/195.2; 210/646; 210/929; 364/705.07; 368/10; 604/4
[58] Field of Search .................. 210/85, 87, 94, 210/138, 646, 929; 364/413.02, 564, 569, 705.07; 368/1, 10, 89, 320, 327, 11, 223, 224; 604/4, 5, 6

[56] References Cited

U.S. PATENT DOCUMENTS

| | | | |
|---|---|---|---|
| 3,598,306 | 8/1971 | Osborne | 368/10 |
| 3,813,533 | 5/1974 | Cone et al. | 364/705.07 |
| 4,022,014 | 5/1977 | Lowdenslager | 364/705.07 |
| 4,035,627 | 7/1977 | Dickinson et al. | 364/705.07 |
| 4,232,382 | 11/1980 | Weinsen et al. | 368/1 |
| 4,267,577 | 5/1981 | Hashimoto et al. | 364/705.07 |
| 4,370,983 | 2/1983 | Lichtenstein | 210/929 |
| 5,247,434 | 9/1993 | Peterson et al. | |

FOREIGN PATENT DOCUMENTS

| | | |
|---|---|---|
| 5682 | 1/1977 | Japan . |
| 3-54590 | 3/1989 | Japan . |
| 2077264 | 3/1990 | Japan . |
| 6-14994 | 1/1994 | Japan . |
| 6-11001 | 3/1994 | Japan . |

*Primary Examiner*—Joseph W. Drodge
*Attorney, Agent, or Firm*—Birch, Stewart, Kolasch & Birch, LLP

[57] ABSTRACT

A water-removal control system for dialysis device includes a volume-setting device for setting a planned volume of water to be removed; a rate-setting device for setting a water-removing rate; and a time-display for calculating from the planned volume of water to be removed, set by said volume-setting device, and the water-removing rate set by said rate-setting device, and for displaying the resultant finish time of dialysis treatment. The control system is so designed as to allow the water-removing rate to be changed step by step by operating the rate-setting device during dialysis, and allow the time-display to calculate the finish time of dialysis treatment synchronously with a stepped change of the water-removing rate as well as to display the resultant finish time of dialysis treatment.

5 Claims, 2 Drawing Sheets

WATER-REMOVAL CONTROL SYSTEM WITH TIMER DISPLAY FOR DIALYSIS DEVICE

BACKGROUND OF THE INVENTION

1. Field of the Invention

The present invention relates to a water-removal control system for dialysis devices and, more particularly, to a water-removal control system capable of recalculating and displaying a planned finish time of dialysis treatment by changing at least one of preset values of a planned water-removing volume and a water-removing rate when there is the necessity of changing a predetermined finish time of dialysis treatment for some reasons or other during dialysis.

2. Description of the Prior Art

Dialysis devices have been used widely to perform dialysis treatment for patients with chronic renal failure. Such dialysis devices are generally composed of a dialyzer, a blood line, a dialysate line, a blood pump, a water-removal pump, and a water-removal control system. The water-removal control system generally comprises a volume-setting means for setting a volume of water to be removed, a rate-setting means for setting a water-removing rate, a control means for controlling water-removing procedure on the basis of a set value of the water-removing rate set by the rate-setting means. The control means is so designed as to calculate a necessary time for dialysis from the set volume to water to be removed and the set value of the water-removing rate, and determine a finish time of dialysis treatment, i.e., a time at which the dialysis treatment has been finished, from the necessary time and the actual time. Generally, the control means is so designed as to have the ability to change the volume of water to be removed and the water-removing rate even in the dialysis treatment.

High performance dialysis devices have recently been developed and make it possible to remove a large volume of water from the blood. However, there is such a fear that the patient's life is in danger because of improper control of water removal which causes excessive or insufficient water removal. Thus, there is an increasing demand for a water-removal control system for dialysis devices that ensures correct and safe control of water removal.

To meet such a demand, a few dialysis devices with a ultrafiltration control system have been proposed, for example, in Japanese Utility Model publication JP-B-6-11001 and Japanese Patent JP-A - 6-14994.

The former discloses a dialysis device comprising a volume-setting means for setting a planned volume of water to be filtered, a rate-setting means for setting a filtering-rate, a control unit for controlling ultrafiltration procedure on the basis of the filtering rate determined by the rate-setting means, the control unit being so designed that it allows at least one of the filtration volume and filtering-rate to be changed during dialysis treatment, the control unit being adapted to calculate the remaining time of dialysis, by using the planned filtration volume, the filtering-rate, and the volume of water filtered by that time, and to display the result. If the filtration volume or filtering-rate is changed during dialysis, the control unit recalculates remaining time of dialysis from the changed value and displays the result.

The latter, JP-A- 6-14994, discloses a water-removal calculating system for dialysis device, including means for setting a planned volume of water to be removed, a planned finish time of dialysis treatment and a current time as data for control of water-removal, and a means for calculating the required time for dialysis treatment from the data, from which the water-removing rate at the time of start of dialysis is calculated automatically. If the dialysis treatment is delayed for some reasons or other, the water-removing rate is automatically recalculated from the remaining time of dialysis treatment and the remaining volume of water to be removed, to eliminate the delay of dialysis treatment, and then reset the water-removing rate to the calculated new value.

However, the dialysis device of JP-B- 6-11001 does not display the finish time of dialysis treatment, but the remaining time of dialysis treatment, so that the operators are liable to make a wrong judgement carelessly on the finish time of dialysis treatment. If it becomes difficult to finish the dialysis treatment within the initially planned time for some reasons or other, there is the necessity of finishing the dialysis treatment within a time shorter than the initially planned finish time. In such a case, the dialysis treatments often bring to an end simultaneously, particularly, when many patients are treated at the same time, so that the operators are pressed by work because of after-treatment and preparation for the next treatments. Accordingly, the operators would make a mistake in calculation when setting the planned volume of water to be removed from the blood or ultrafiltration rate.

Since the water-removal calculating system of JP-A-6-14994 is so designed as to reset the water-removing rate to finish the dialysis treatment at the initially determined time, the water-removing rate becomes too fast, causing excess water-removal. This problem may be overcome by setting upper limits to the water-removing rate, but it requires recalculation of the water-removing rate every time the water-removing rate exceeds the limit.

SUMMARY OF THE INVENTION

It is therefore an object of the present invention to provide a water-removal control system for dialysis devices, which causes no excess water-removal and makes it possible to control schedules of dialysis treatment so as to be free from concurrent finishes of dialysis treatments.

The above and other objects of the present invention are achieved by providing a water-removal control system for dialysis device, including:

a volume-setting means for setting a planned volume of water to be removed or a planned water-removing volume;

a rate-setting means for setting a water-removing rate; and a time-displaying means for calculating from the planned volume of water to be removed, set by said volume-setting means, and the water-removing rate set by said rate-setting means, and for displaying the resultant finish time of dialysis treatment;

said control system being so designed as to allow the water-removing rate to be changed step by step by operating the rate-setting means during dialysis, and allow the time-displaying means to calculate the finish time of dialysis treatment synchronously with a stepped change of the water-removing rate as well as to display the resultant finish time of dialysis treatment.

In a preferred embodiment, the rate-setting means is composed of an up and down type switch or a pair of push-button switches.

The control system may be so designed as to allow the planned water-removing volume to be changed step by step by operating the volume-setting means during dialysis, and to allow the time-displaying means to calculate the finish time of dialysis treatment synchronously with a stepped change of the planned water-removing volume as well as to display the resultant finish time of dialysis treatment. In this case, the volume-setting means for setting the planned water-removing volume is preferably composed of an up-down type switch or a pair of push-button switches.

In still another embodiment, the control system is provided with a displaying means for calculating and displaying a remaining time from the actual time to the planned finish time of dialysis treatment.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The above and other objects and features of the present invention will become clear from the following description taken in conjunction with the preferred embodiments thereof with reference to the accompanying drawings which are given by way of illustration only, and thus are not limitative of the present invention, and throughout which like parts are designated by like reference numerals, and in which.

DETAILED DESCRIPTION OF THE PREFERRED EMBODIMENTS

Figure 1:
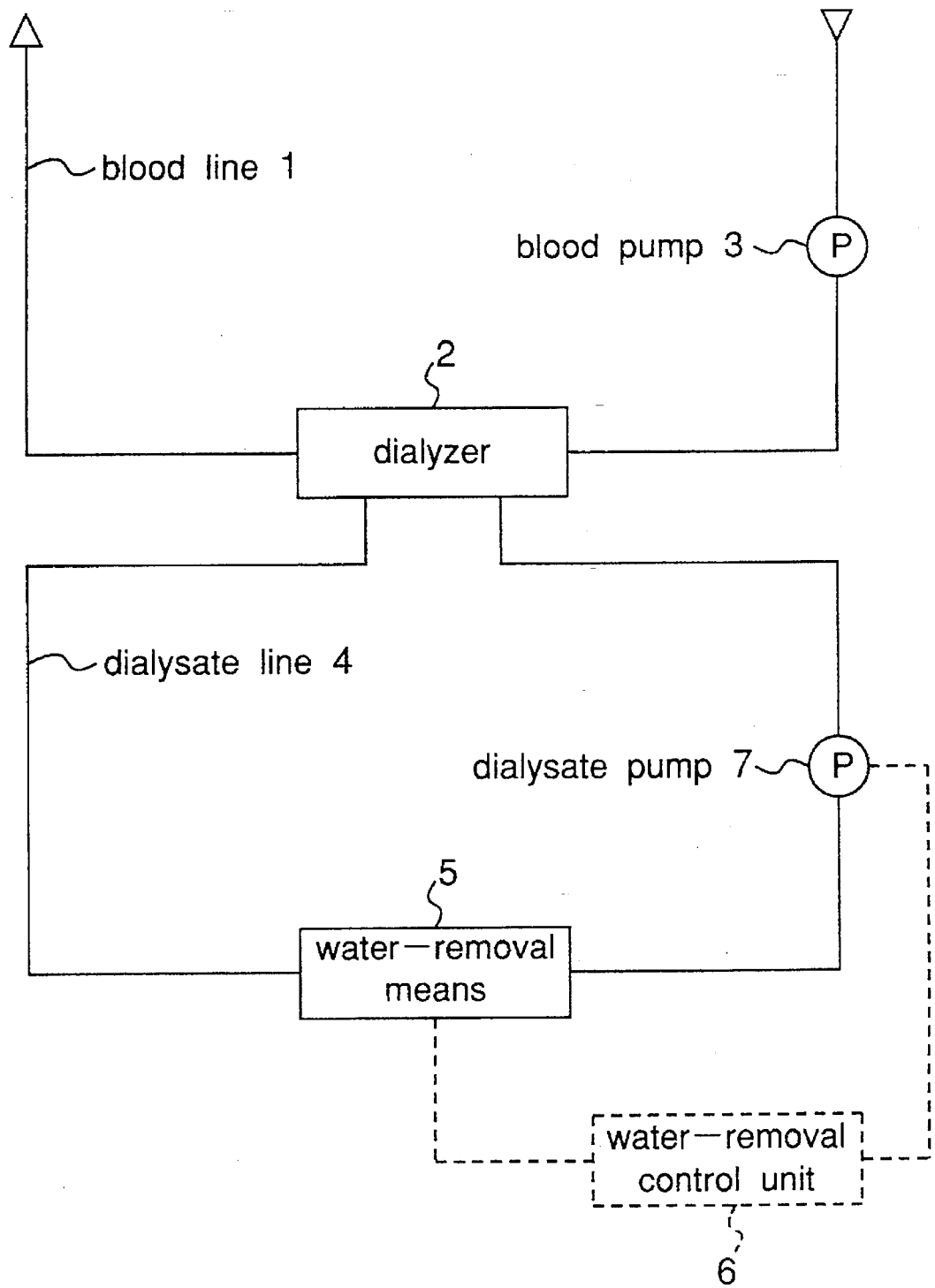
FIG. 1 is a diagram illustrating a dialysis device with a water-removal control system according to the present invention.

Referring to FIG. 1, there is shown a hemodialysis system comprising blood line 1, a dialyzer 2 arranged in the blood line 1, a blood pump 3 arranged in an upstream side of the blood line 1, a dialysate line 4 connected to the dialyzer 2, a water-removing means 5 arranged in the dialysate line 4 to remove water from the blood, a dialysate pump 7 for feeding a dialysate to the dialysate-line 4, and a water-removal control unit 6 for controlling the water-removing means 5 and dialysate pump 7.

During dialysis, the blood from the vein of a patient is introduced into the dialyzer 2 by the blood pump 3 via the blood line 1, and the dialysate is introduced into the dialyzer 2 by the dialysate pump 7 via the dialysate line 4 to remove toxic wastes and surplus water from the blood. In the dialyzer 4, the blood is dialyzed and then returned to the artery of the patient via the blood line 1. At that time, the surplus water in the blood is removed therefrom at a predetermined rate, introduced along with the waste dialysate into the water-removing means 5 through the dialysate line 4, and then discharged out of the system. During dialysis, the water-removing rate of the water-removing means 5 and the operation of the dialysate pump 7 are controlled by the control unit 6.

After starting the dialysis treatment, it might be necessary to increase the water-removing rate to catch up the delay of dialysis treatment because of interruption of the water removal control due to warning signals, or it might be necessary to change the finish time of dialysis treatment because of fears that it might cause extremely hard work resulting from concurrent finish of the dialysis treatments of many patients. Further, it might be necessary to change the planned volume of water to be removed. The water-removal control system of the present invention is so designed as to meet such requirements by changing the water-removing rate. Further, the water-removal control system of the present invention may be so designed as to have a function to respond to these requirements by changing the planned water-removing volume.

In this embodiment, the control system is so designed that the value of the water-removing rate can be changed step by step by operating the rate-setting means (switch 9) even when the dialysis treatment is being carried out. To this end, the rate-setting means is composed of a pair of up and down key switches. Also, the volume-setting means is composed of a pair of up and down key switches so as to make it possible to change the value of the volume of water removal step by step during dialysis.

The water-removing means 5 is generally composed of a ultrafiltration pump as disclosed in JP-B- 56-82 or a device as disclosed in JP-B- 3-54590. The device disclosed in JP-B- 3-54590 comprises a closed container for temporarily storing fresh and used dialysate, the closed container being partitioned by two movable diaphragms into a dialysate feed chamber, a dialysate recovery chamber, and a variable-volume chamber located between them and connected to a volume-control means containing a silicone oil and forcing it to flow into or flow out from the variable-volume chamber to control its volume.

Figure 2:
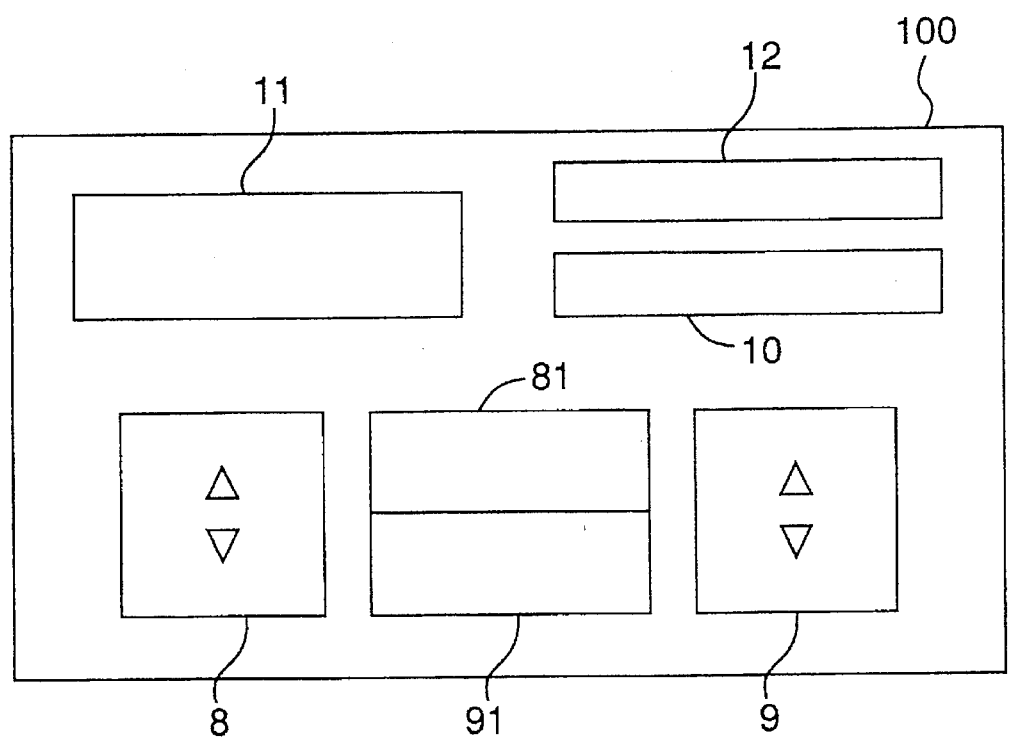
FIG. 2 is a diagram illustrating one example of a display panel of a water-removal control unit of FIG. 1.

The water-removal control unit 6 includes a microprocessor (not shown) that performs arithmetic and logical calculations and controls the operations of the other elements of the system. Also, the control unit 6 includes a display panel 100 as shown in FIG. 2, which is provided with input means for setting data required for control of water removal and a means for displaying control data as the occasion demands. Data required for control of water removal generally include, for example, a planned volume of water to be removed from the blood, a water-removing rate, and a planned finish time of dialysis treatment.

As shown in FIG. 2, the display panel 100 in this embodiment is provided with a volume-setting switch 8 for setting a planned volume of water to be removed, a rate-setting switch 9 for setting a water-removing rate, three basic displaying windows (81, 91 and 12), and additional two displaying windows (10 and 11). The displaying window 81 is used for displaying the planned volume of water to be removed that has been set by the volume-setting switch 8, the displaying window 91 is for displaying the water-removing rate set by the rate-setting switch 9, and the displaying window 12 is for displaying the planned finish time of dialysis treatment which had been derived from the planned water-removal volume and the water-removing rate by the microprocessor. One of the additional displaying windows 10 is used for displaying an elapsed time from the beginning of the dialysis treatment, while the other additional displaying windows 11 is for displaying an actual or current time. The additional displaying windows 10 and 11 are optional and thus they may be omitted if unnecessary.

If necessary, the display panel 100 may be provided with a remaining-time displaying means including an additional window for displaying a time period between the actual time and planned finish time of dialysis treatment. The provision of the remaining-time displaying means makes it possible to modify the schedule of dialysis treatment with ease when treating many patients at the same time, since the remaining time for each patient can be seen at a glance.

In use, a planned water removal volume is set first by pushing the volume-setting switch 8, and then the water-removing rate is set by the rate-setting switch 9. These set values are respectively displayed in the displaying windows 81 and 91 and a required time for dialysis treatment is automatically determined from set values of the planned volume and the water-removing rate by equation:

Required time=planned volume/water-removing rate

Then, from the required time and the actual time, a finish time of dialysis treatment is automatically calculated by the control unit 6 and displayed in the finish time-displaying window 12.

If there is the necessity of changing the water-removing rate or planned finish time of dialysis treatment during dialysis, this may be done by changing the set value of water-removing rate. If there is the necessity of changing the initially planned volume of water to be removed, this may be done by operating of the rate-setting switch 9. If an upper or lower half of the push button switch 9 is pressed and held under pressed condition, the water-removing rate is increased or decreased step by step and simultaneously displayed in the water-removing rate displaying window 91. At the same time, a newly estimated finish time of dialysis treatment is recalculated and displayed as a new planned finish time of dialysis treatment in the displaying window 12.

The change of the finish time of dialysis treatment can be carried out by pressing the rate-setting switch 9 and holding it under the pressed condition until the finish time of dialysis treatment displayed in the displaying window 12 reaches to the desired finish time of dialysis treatment. Thus, it is easy to modify the finish time of dialysis treatment during dialysis. Further, it is possible to avoid the calculation error or input error of the water-removing rate or finish time of dialysis treatment during dialysis.

By previously storing an upper limit of the water-removing rate for each patient in the memory of the water-removal control unit 6, it is possible to avoid excess water-removal since the control unit prevents the water-removing rate from being increased over the upper limit even if the push button switch is being pressed after the water-removing rate has reached to the upper limit. Of course, the indication of the finish time of dialysis treatment is not altered after the water-removing rate has reached to the upper limit.

Further, the planned finish time of dialysis treatment can be changed by adjusting the volume of water to be removed. This may be done in the same manner as above procedure, for example, by pressing an upper or lower half of the volume-setting switch 8.

The control system of the present invention may be provided with a means for displaying the remaining time of dialysis treatment calculated by the control unit. In this case, the remaining time of dialysis treatment is indicated in the displaying window. The longer the remaining time, the wider the range of variation of the finish time of dialysis treatment. Thus, it is convenient to use the remaining time displaying means when there is the necessity of shortening the required time for dialysis treatment or of catching up the delay of dialysis treatment during dialysis.

As will be understood from the above, according to the present invention, it is possible to schedule the finish time of dialysis treatment, thus making it possible to avoid concurrent finish of the dialysis treatments for many patients. Further, according to the present invention, it is possible to provide a control system which is easy to control the finish time of dialysis treatment, free from calculation errors and free from fears that it might cause excess removal of water when the water-removing rate is changed during dialysis.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A dialysis device comprising means for performing dialysis treatment and a water-removal control system the control system including:

volume-setting means for setting a planned volume of water to be removed by the device;

rate-setting means for setting a water-removing rate; and time-displaying means for calculating from the planned volume of water to be removed, set by said volume-setting means, and the water-removing rate set by said rate-setting means, and for displaying the resultant finish time of dialysis treatment;

said control system being so designed as to allow the water-removing rate to be changed step by step by operating the rate-setting means during dialysis, and allow the time-displaying means to calculate the finish time of dialysis treatment synchronously with a stepped change of the water-removing rate as well as to display the resultant finish time of dialysis treatment.

2. The water-removal control system for dialysis device according to claim 1, wherein the rate-setting means is comprised of an up and down type switch.

3. The water-removal control system for dialysis device according to claim 1, wherein the control system is so designed as to allow the planned water-removing volume to be changed step by step by operating the volume-setting means during dialysis, and to allow the time-displaying means to calculate the finish time of dialysis treatment synchronously with a stepped change of the planned water-removing volume as well as to display the resultant finish time of dialysis treatment.

4. The water-removal control system for dialysis device according to claim 3 wherein the volume-setting means is comprised of an up and down type switch.

5. The water-removal control system for dialysis device according to claim 1, wherein said control system includes displaying means for calculating and displaying a remaining time from the actual time to the finish time of dialysis treatment.

* * * * *

UNITED STATES PATENT AND TRADEMARK OFFICE
CERTIFICATE OF CORRECTION

PATENT NO. : 5,656,153
DATED : August 12, 1997
INVENTOR(S) : Kameno et al.

It is certified that error appears in the above-indentified patent and that said Letters Patent is hereby corrected as shown below:

On the title page: Item [30] left column, change the Priority Date to correctly read:

--June 10, 1994--.

Signed and Sealed this

Twenty-third Day of June, 1998

Attest:

BRUCE LEHMAN

Attesting Officer

Commissioner of Patents and Trademarks